United States Patent
Fladda et al.

(10) Patent No.: US 6,929,715 B2
(45) Date of Patent: Aug. 16, 2005

(54) METHOD AND A DEVICE FOR MEASURING CONCENTRATIONS

(75) Inventors: Gerdt Fladda, Täby (SE); Jonny Weng, Säffle (SE)

(73) Assignee: BTG Källe Inventing AB, Säffle (SE)

( * ) Notice: Subject to any disclaimer, the term of this patent is extended or adjusted under 35 U.S.C. 154(b) by 314 days.

(21) Appl. No.: 10/349,922

(22) Filed: Jan. 24, 2003

(65) Prior Publication Data

US 2003/0141029 A1 Jul. 31, 2003

(30) Foreign Application Priority Data

Jan. 25, 2002 (SE) .............................................. 0200221

(51) Int. Cl.⁷ .............................................. D21F 13/00
(52) U.S. Cl. ...................... 162/198; 162/263; 73/61.41; 73/64.56
(58) Field of Search ................................ 162/198, 263; 73/61.41, 64, 56

(56) References Cited

U.S. PATENT DOCUMENTS

| | | | | |
|---|---|---|---|---|
| 3,718,030 A | * | 2/1973 | Kesler ........................ 73/61.72 |
| 3,838,594 A | * | 10/1974 | Kesler ........................ 73/61.72 |
| 3,869,922 A | * | 3/1975 | Fajans et al. .................. 73/438 |
| 4,409,853 A | * | 10/1983 | Chase et al. ................... 73/863 |
| 4,635,470 A | * | 1/1987 | Skallen et al. .............. 73/53.04 |
| 4,840,047 A | * | 6/1989 | Richter et al. ............ 68/181 R |
| 4,881,286 A | * | 11/1989 | Richter et al. ................. 8/156 |
| 5,319,987 A | * | 6/1994 | Vassel ...................... 73/863.71 |
| 5,536,942 A | * | 7/1996 | Barringer et al. ...... 250/339.12 |
| 5,736,654 A | * | 4/1998 | Dubois ..................... 73/863.84 |

* cited by examiner

*Primary Examiner*—Mark Halpern
(74) *Attorney, Agent, or Firm*—Dickstein Shapiro Morin & Oshinsky LLP

(57) ABSTRACT

A method and a device for measuring concentrations especially in a pulp suspension, from which a sample has been taken. The sample is collected in a measuring vessel, in which a piston is guided upwards and downwards in order to press the sample from each direction through a measuring sensor collected at the side of the measuring vessel via communicating tubes connected in an upper and a lower position to the measurement vessel, whereby the sample is stirred totally to eliminate flocculation in the same. Measurement of the concentration of the sample is made either during the upwards and downwards movement of the piston in the measuring vessel and first occurs when the speed of the sample through the measuring sensor is constant and the sample has been homogenized after at least some movement upwards and downwards of the piston.

8 Claims, 2 Drawing Sheets

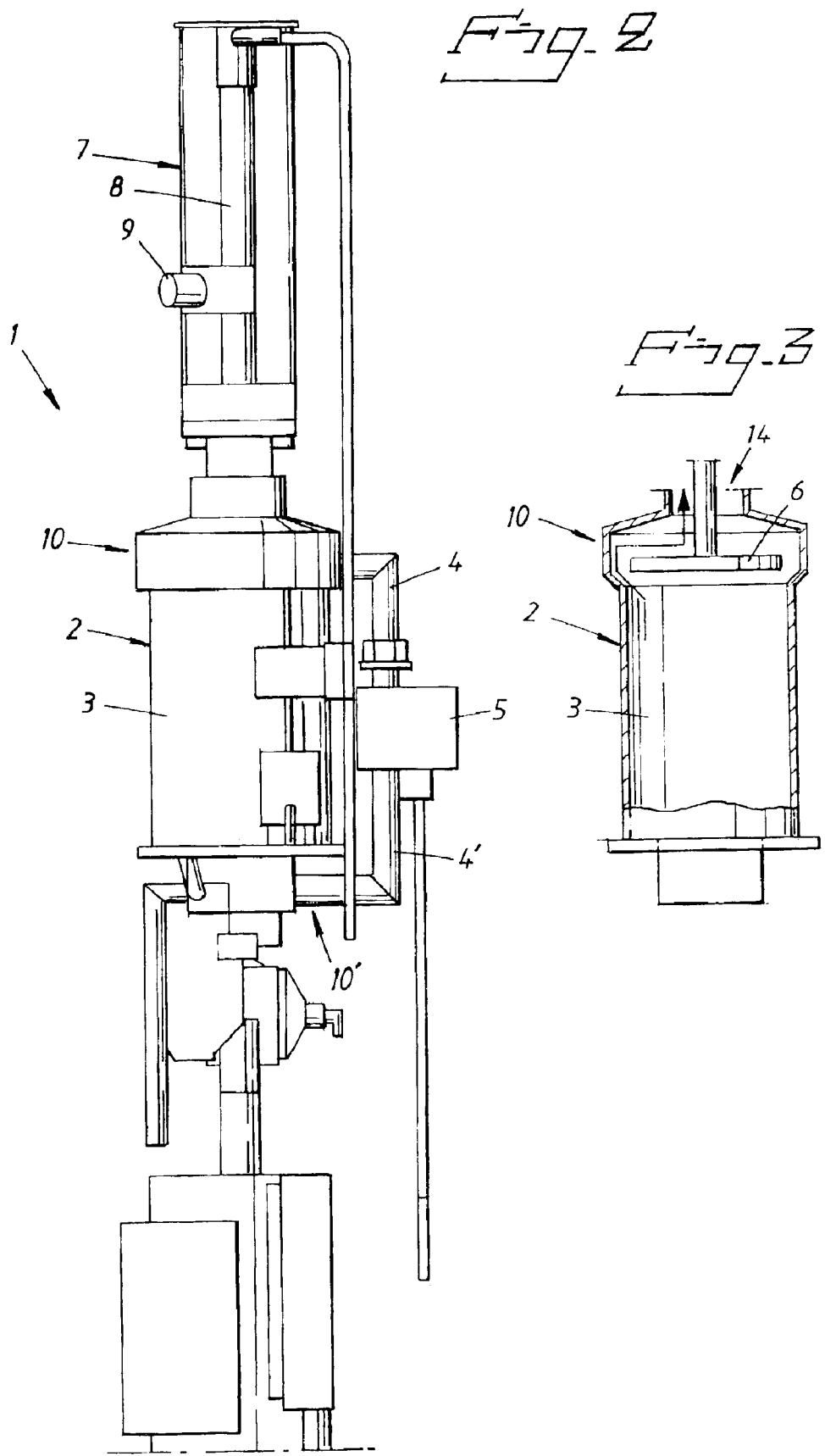

METHOD AND A DEVICE FOR MEASURING CONCENTRATIONS

This application claims priority to application 0200221-0 filed in Sweden on Jan. 25, 2002.

BACKGROUND OF THE INVENTION

1. Field of the Invention

The present invention refers to a method and a device for measuring concentrations preferably in pulp suspensions.

2. Description of the Related Art

Better control over processes in manufacturing industry is one solution in order to obtain a better productivity, better and new qualities and less influence on the surroundings. Therefore measuring on-line is absolutely a necessity. The measurement shows the connections between the process, the raw material and the finished product and gives an increased understanding for the dynamic of the process and with that a basis for taking up more effective control strategies. Measuring on-line can be done in different ways depending on the measuring method and the measuring sequence required. One method is measuring in-line where the measuring sensor is directly mounted in the measuring medium, e.g. a temperature sensor. However, specific measuring parameters often have to be determined on samples taken out from the measuring medium. One reason for this is that the sample before the measuring procedure e.g. has to be diluted to lower concentrations or be pre-treated in another way, for example pH-adjusting, de-airation, dosing of chemicals in order to initiate certain reactions, which thereafter shall be measured etc.

Within pulp- and paper industry concentration measuring on pulp suspensions is of a central importance. These suspensions often contain not only wood fibres but also different fill agents such as clay, calcium carbonate etc. and various chemicals for example for bleaching of the fibres or flock formation between the different suspended substances. Dependent on the measuring position the concentration can vary between one tenth of a procent and ten procent. In certain measuring positions it is extra important to obtain accurate results on the total concentration of fibres inclusive filler, and also on only filler. An in-line meter cannot always give such an information. This can depend on the state of the suspension and/or on the actual design of the method, which is not suitable to base an in-line sensor upon.

For concentration measuring optical measuring principles are often used, especially when differentiated information concerning the composition of the suspension with respect to different suspended materials, shall be obtained. Optic concentration measuring is among other things sensitive for air bubbles in the suspension and flock formation. Flocks constitute "large particles" of many small and give an incorrect measurement signal information. In situations having among other things the criteries mentioned above a special sample treatment equipment is used in order to obtain a satisfactory results. The equipment normally consists of a measuring vessel having an integrated pump loop, in which the measuring sensor is placed. The principle function is as follows: Via a sampling valve a separate pulp sample is fed to the measuring vessel and is thereafter pumped around a certain time before the measuring is made. The pumping around of the sample before the measuring is needed so that the sample shall be de-aired and de-flocculated. After the measurement the sample is drained from the measuring vessel to the outlet and the next measuring cycle is started in that a new sample is taken. Between a number of measurements the whole sample treatment unit can be cleaned by water distributors and filling up with clean water. Besides a measurement can be done on the clean water in order to zero point calibrate the optical measuring system. At too high concentrations the optical measuring principle does not function satisfactory and there is in this case a risk that the measuring cell is plugged by the pulp. Therefore, the sample, when needed, be diluted with clean water. The dilution is controlled via level guards in the measuring vessel.

The conventional method which is here described for a sample treatment unit in connection with for example an optical concentration determination of pulp suspensions functions on the whole. However, there are evident limitations and/or drawbacks:

For the task a relatively big, expensive and energy requiring pump is needed, which besides must be rotation speed regulated in order to obtain a suitable flow rate for the measurement through the measuring transducer and for control of the deaeration. A too high rotation speed instead can create a vortex formation in the measuring vessel, so that air is sucked into the suspension.

The tightening between the motor axle and the pump housing becomes easily untight and relatively often has to be changed. The untightness means that air can be sucked into the suspension, which shall be measured, which spoils the measurement.

The fibres of the pulp suspension in the pump housing can be broken or in another way be changed, so that the measuring results can be wrong. Furthermore, during high rotation speeds in the pump housing cavitation effects can easily arise, so that disturbing air bubbles are created. Dependent on the structure the pump housing can also be difficult to be deaerated at the time of each new measurement cycle.

A pump based sample treatment unit requires a relatively large measuring vessel. The size of the measuring vessel is directly related to the deaeration and deflocculation time and to that time it takes to homogenize the sample, especially when diluted, which is of great importance for the quality of the measurement. Prolonged times also mean that the total time for a whole measurement sequence is prolonged, so that the measurement frequency is too low in order to receive a good control information for an effective process control.

SUMMARY OF THE INVENTION

The object of the present invention is to provide a new type of sample treatment unit, which eliminates the drawbacks stated above, which exist in a pump based system. The features characterizing the invention appear from the subsequent patent claims.

Thanks to the invention there do now exist a method and a device for measurement of concentration of especially pulp suspensions, said device is essentially cheaper, simpler in its structure, more reliable in running and has a larger efficiency concerning stirring/homogenizing, deaearation and deflocculation. All this gives a quicker, better and run-safer measuring information.

BRIEF DESCRIPTION OF DRAWINGS

The invention will now be described in more detail below by aid of a preferred embodiment example with reference to the drawings enclosed, on which FIG. 2 illustrates the sample treatment unit in FIG. 1 turned 90° without the connected vessel for dilution of the measurement sample and FIG. 3 is a schematic side-view of the measuring vessel of the sample treatment unit having its piston in its upper position.

DETAILED DESCRIPTION OF THE INVENTION

Figure 1:
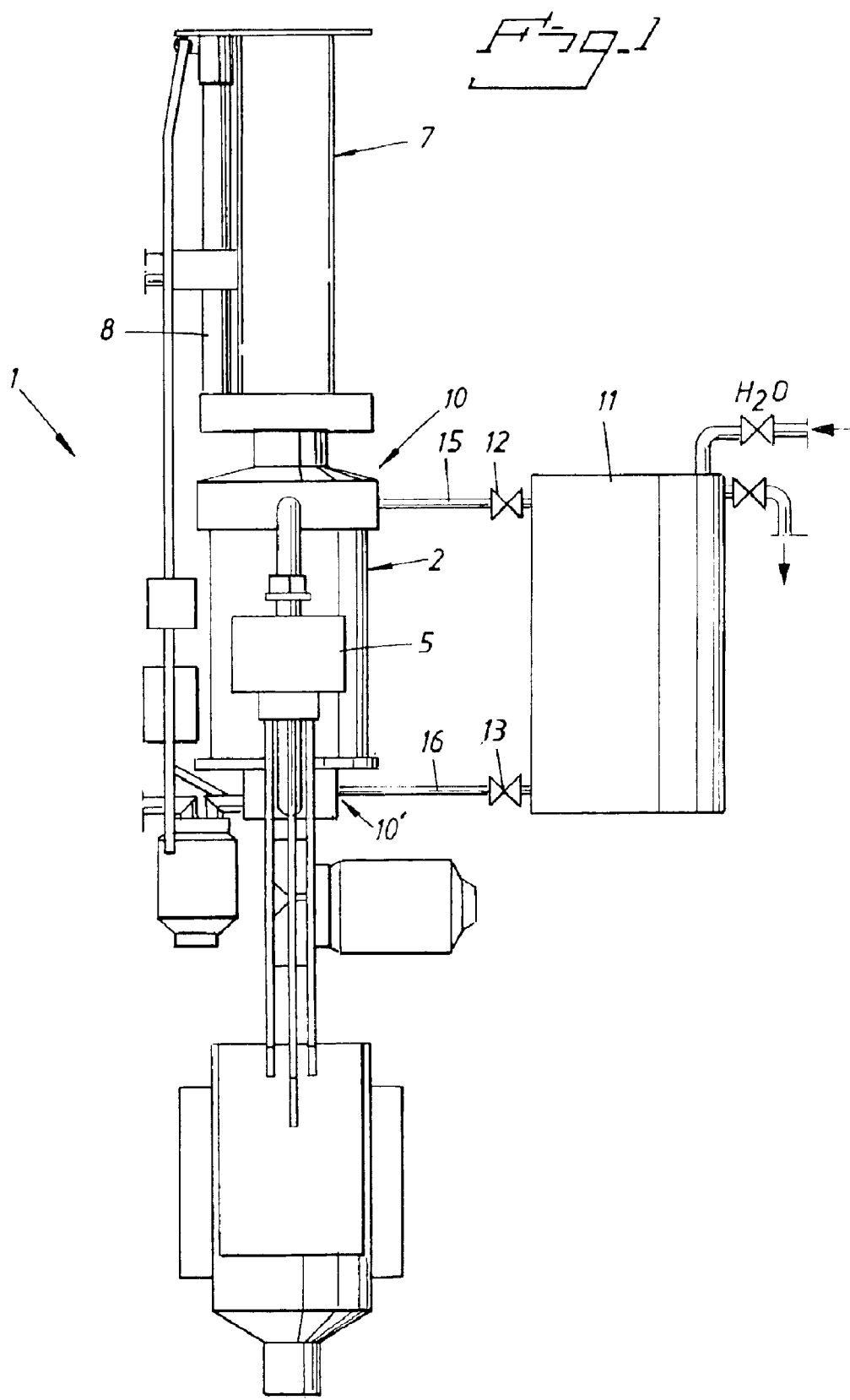
FIG. 1 illustrates a side-view of a sample treatment unit according to the invention, having a connected vessel for dilution of the measuring sample with clean water.

As can be seen from the drawings the invention refers to a device in the form of a sample treatment unit 1, which is based on a closed measuring vessel 2, which is filled completely with a measuring sample 3. At the side of the measuring vessel 2, which in the example illustrated is cylinderformed, communicating tubes 4 and 4' are provided, which connect the upper part 10 and the lower part 10' of the measuring vessel 2 to a measuring sensor 5. A piston 6 is guided upwards and downwards in the measuring vessel 2 via a pressure air cylinder 7, so that the measuring sample 3 is pressed through the measuring sensor 5 from each direction. The diameter of the piston 6 is mainly the same as the inner diameter of the measuring vessel 2. The flow rate is in a simple way controlled via the speed of the piston 6, which in its turn is controlled via the pressure of the used pressurized air, regulated by aid of a pressure reducing wave. The measurement can be done both during the movement upwards and downwards of the piston 6 and is made only when the speed of the sample 3 through the measuring sensor 5 is constant and the sample 3 at least after some movement upwards or downwards of the piston 6, has been homogenized. The arrangement of the measuring vessel and the piston gives a 100% movement or transport of the total measuring volume of the taken sample and a quick and effective stirring and deflocculation of the sample, so that a representative measurement sample can be supplied to the sensor for the measurement. Furthermore the transport of the measuring sample 3 cannot provide any changement of the fibres of the measurement suspension, which in a contrast hereto can be the case using a pump according to the prior art described above. Stirring and deflocculation is provided according to the invention by a strong turbulent formation, when the sample 3 at the lower- and upper side of the measuring vessel 2, respectively, is pressed into the communicating tubes 4,4' located at the side of said measuring vessel 2, which includes the measuring sensor 5. The deaeration of the measuring sample 3 occurs via an deaeration pipe 8 mounted to the upper side of the measuring vessel 2. The upper part 10 of the measuring vessel 2 is provided with larger, inner diameter than the rest of the same, so that air bubbles can move upwards and disappear through the deaeration pipe 8, whereby air bubbles can pass the piston 6, when it is in its uppermost position. During filling of the measuring vessel 2 with the sample 3 the piston 6 is normally in its uppermost position, so that an immediate deaearation shall take place, however, also so that the measuring vessel 2 totally can be filled with the pulp suspension. A level sensor at the deaearation pipe indicates that the measuring vessel 2 is filled up and that the in-flow of the measuring sample 3 in this case can be stopped, so that thereafter the measuring sequence can be started.

Another advantage with the unit according to the invention is that plugging of the measuring sensor 5, which normally has a smaller feeding flow area than the area of the communicating tubes 4 and 4' on the side of the measuring vessel, easily can be prevented by turning the movement direction of the piston 6, so that the "mass plug" both can be sucked and pressed "in right direction" out from the sensor opening. A plugging of the measuring sensor 5 is indicated in a simpler way via the speed change of the piston 6 and/or via a built-in pressure transmitter. The speed of the piston 6 can be calculated via the time it takes to move the pneumatic cylinder 7, which is used for control of the piston 6 from the one to the other end position. This movement or displacement is indicated by aid of an end position sensor, which is used in order to change direction of the piston during the movement of the same in an upward and downward direction. For dilution of measuring sample 3 a communicating vessel 11 containing clean water is used in parallel with the measuring vessel 2. This dilution vessel 11 is via valves 12,13 and pipes 15,16 connected to the measuring vessel 2. If both the upper and the under valves 15 and 16 are opened the undiluted sample is mixed quickly and effectively with the water, especially if the dilution vessel 11 is not bigger in its volume than the measuring vessel 2.

What is claimed is:

1. A method for measuring concentration especially in a pulp suspension, from which a sample has been taken, characterized in that the sample (3) is collected in a measuring vessel (2), in which a piston (6) is guided upwards and downwards in order to press said sample (3) in the upwards and downwards direction through a measuring sensor (5) connected at the side of the measuring vessel via communicating tubes (4,4') connected in an upper and lower position to the measuring vessel (2), whereby the sample (3) is stirred totally for eliminating flocculation in the sample, whereupon a measurement of the concentration of the sample (3) is made either during upward movement or downward movement of the piston (6) in the measuring vessel (2); and wherein measurement of the concentration of the sample is made only when the speed of the sample (3) through the measuring sensor (5) is constant and the sample (3) has been homogenized as a result of the upwards and downwards movement of the piston.

2. The method according to claim 1, characterized in that the sample (3) is subjected to a strong turbulent formation during its pressing by aid of the piston laterally into the communicating tubes (4,4') locataed at an upper-side and an underside of the measuring vessel (2), respectively.

3. The method according to claim 1, characterized in that the sample (3) is deaerated before the measurement of the concentration via at least one deaeration pipe (8) provided on an upper side of the measuring vessel (2).

4. The method according to cloaim 1, characterized in that the sample (3) is diluted with clean water from a vessel (11) which is provided to the measuring vessel (2) via valves (12,13).

5. A device for measuring concentrations especially in a pulp suspension, from which a sample (3) has been taken and including a measuring vessel (2) for collecting the sample (3), characterized in that the measuring vessel (2)is included in a sample treatment unit (1), which via communicating tubes (4,4') connect an upper (10) and lower portion (10') of the measuring vessel to a measuring sensor (5), in which a piston (6) is movable upwards and downwards in order to press the sample (3) through the measuring sensor (5) in upwards and downwards directions and said diameter of said piston (6) substantially corresponds to the inner contour of the measuring vessel (2), the flow rate of the sample (3) being controlled by the speed of the piston (6) and the measurement of the concentration of the sample can be taken during both the upwards and downwards movement of the piston (6), said measurement not taking place until the speed of the sample (3) through the measuring sensor (5) is constant and the sample (3) has been homogenized.

6. The device according to claim 5, characterized in that measuring vessel (2) has the form of a cylinder having a diameter which mainly corresponds to the diameter of the displaceable piston (6) in the measuring vessel.

7. The device according to claim 5, characterized in that the upper portion (10) of the measuring vessel (2) has a larger inner diameter than the rest of the measuring vessel (2) (14) to allow air bubbles to pass the piston and travel up to an deaeration pipe (8) located on the measuring vessel.

8. The device according to claim 5, characterized in that the measuring vessel (2) has a dilution vessel (11) with clean water provided in parallel with the same, said vessel (11) communicates with the measuring vessel with tubes (15,16) via valves (12,13).

* * * * *